US012629030B2

(12) United States Patent
De Vries

(10) Patent No.: US 12,629,030 B2
(45) Date of Patent: May 19, 2026

(54) SYSTEM AND METHOD FOR DETERMINING VIBRATION AMPLITUDES OF A STRUCTURAL ELEMENT OF THE EAR

(71) Applicant: Acoustic Insight B.V., Delft (NL)

(72) Inventor: Haaije Rimmer De Vries, Delft (NL)

(73) Assignee: Acoustic Insight B.V., Delft (NL)

( * ) Notice: Subject to any disclaimer, the term of this patent is extended or adjusted under 35 U.S.C. 154(b) by 190 days.

(21) Appl. No.: 18/274,084

(22) PCT Filed: Jan. 25, 2022

(86) PCT No.: PCT/EP2022/051612
§ 371 (c)(1),
(2) Date: Jul. 25, 2023

(87) PCT Pub. No.: WO2022/157382
PCT Pub. Date: Jul. 28, 2022

(65) Prior Publication Data
US 2024/0415390 A1      Dec. 19, 2024

(30) Foreign Application Priority Data
Jan. 25, 2021    (NL) ...................................... 2027382

(51) Int. Cl.
*A61B 5/00* (2006.01)

(52) U.S. Cl.
CPC .......... *A61B 5/0066* (2013.01); *A61B 5/0051* (2013.01); *A61B 5/7235* (2013.01)

(58) Field of Classification Search
CPC ... A61B 5/0066; A61B 5/0051; A61B 5/7235; A61B 5/125; A61B 5/6815; A61B 2576/02
See application file for complete search history.

(56) References Cited

U.S. PATENT DOCUMENTS

2013/0060131 A1    3/2013   Oghalai et al.
2015/0148654 A1    5/2015   Whanwook et al.
(Continued)

FOREIGN PATENT DOCUMENTS

WO      WO-2019068195 A1 *   4/2019   ............. A61B 5/004

OTHER PUBLICATIONS

R. Paschotta, "Interferometers". RP Photonics Encyclopedia. archived May 22, 2012. (Year: 2012).*
(Continued)

*Primary Examiner* — Tarifur R Chowdhury
*Assistant Examiner* — Paul Schnase
(74) *Attorney, Agent, or Firm* — Patterson + Sheridan, LLP

(57) ABSTRACT

The invention provides a system for determining vibration amplitudes of a structural element of the ear, comprising: an acoustic stimulator, configured to generate an acoustic stimulus having an acoustic period to induce vibrations of the structural element; at least one OCT device, configured to measure a measurement signal representative for relative positions of measurement points on the structural element during the vibrations by projecting a measurement beam on the measurement points and to measure a reference signal representative for a motion phase of the structural element by projecting a reference beam on a reference point on the ear; and a processing unit, configured to determine vibration amplitudes of the measurement points on the basis of the reference signal and the measurement signal, wherein the projections of the measurement beam and the reference beam are related in time, such that a motion phase represented in the reference.

16 Claims, 6 Drawing Sheets

(56) References Cited

U.S. PATENT DOCUMENTS

2020/0060583  A1*   2/2020   Macdougall ......... A61B 5/0066
2023/0380725  A1*  11/2023   Yelin ..................... A61B 5/126

OTHER PUBLICATIONS

Netherlands Search Report and Written Opinion dated Oct. 13, 2021, for Netherlands Patent Application No. 2027382.
PCT International Search Report and Written Opinion dated May 30, 2022, for International Application No. PCT/EP2022/051612.

* cited by examiner

SYSTEM AND METHOD FOR DETERMINING VIBRATION AMPLITUDES OF A STRUCTURAL ELEMENT OF THE EAR

FIELD OF THE INVENTION

The present invention relates to a system for determining vibration amplitudes of a structural element of the ear, a method for determining vibration amplitudes of a structural element of the ear, and use of the system for determining vibration amplitudes of a structural element of the ear.

BACKGROUND OF THE INVENTION

OCT, or optical coherence tomography, enables vibrographic measurements of parts of the ear, such as the eardrum or ossicles, at a sampling rate much higher than the speed of sound, for example at 100 kHz-1 MHz. To determine vibrations of a part of the ear with OCT, movements of that part of the ear may be measured in response to an external stimulus, such as a sound wave. The characteristics of the oscillation provide clinically relevant information on the basis of which properties of the part of the ear can be determined, such as a degree of functioning.

The stimulated part of the ear will normally vibrate with a frequency that corresponds to the frequency of the external stimulus. In particular, the amplitude or maximum displacement of the part of the ear, with respect to a rest position, due to the vibration depends, among other things, on the properties of the tissue. Therewith, the amplitude provides important information about the part of the ear. In order to determine the amplitude, it is usually necessary to link the acoustic stimulus and the measurement to each other.

An OCT system and an acoustic stimulus may be linked by simultaneous activation through a trigger signal. An example is known from WO2017063090, wherein the acoustic stimulus is generated using the sweep trigger of the light source, such that the waveform of the acoustic stimulus is generated in correspondence with each A-scan of the OCT system.

A disadvantage of activating the measurement and the acoustic stimulus according to a trigger is, although the phase of the acoustic wave, when emitted, may be known, the phase of the acoustic wave of the acoustic stimulus, when reaching the part of the ear to be measured, is not known. As the speed of sound of the acoustic stimulus is lower than the speed of light of the OCT system, this unknown difference in phases causes a discrepancy in the measurements, which is further aggravated by variation in the distance between the part of the ear and the OCT system and/or the acoustic source. This distance may vary, for example, between 10-30 mm, which, at a speed of sound of 343 m/s, is equivalent to a variation of 0.06 ms. At an acoustic frequency of 1000 Hz, this may lead to a phase error of over 21°, and an error of more than 210° at 10000 Hz.

Even if the acoustic wave would be measured closer to the ear, for example with a microphone, the acoustic wave, or a reflection thereof, would not be measured at an optimal position: namely not on the part of the ear to be measured. An additional disadvantage is that echoes or secondary reflections of the acoustic stimulus from parts of the ear other than the structural element of interest could not be excluded.

Another approach to determine a vibration amplitude of a structural element is to measure a measurement point of interest during at least one full acoustic period, preferably several acoustic periods, wherein the large number of measurements over a longer measurement time would increase the chance that the (maximum) amplitude is measured.

The disadvantage is that for each point to be measured on the part of the ear, several acoustic periods need to be measured in order to determine an amplitude with sufficient certainty. This would take a very long time when multiple measurement points are to be measured. For example: when measuring a surface consisting of a 500×500 grid of measurement points, with an acoustic stimulus of 1000 Hz (1 ms for a single acoustic period), measuring 10 acoustic periods for each measurement point would require 2500 seconds, or more than 40 minutes.

Therefore, known techniques are not suitable for measuring vibrations of larger areas of the ear precisely and within a reasonable timespan.

Object of the Invention

It is an object of the present invention to provide an improved system and method for determining vibration amplitudes of a structural element of the ear, which overcomes one or more of the disadvantages of the prior art, or at least to provide an alternative system and method for determining vibration amplitudes of a structural element of the ear.

The Present Invention

The present invention provides a system for determining vibration amplitudes of a structural element of the ear according to claim 1.

According to the present invention, an acoustic stimulus is generated to induce vibrations of the structural element. The vibration motion causes displacements of the structural element, which vary according to an acoustic period of the acoustic stimulus and which may vary over the structural element.

A measurement signal is measured using a measurement beam projected on multiple measurement points on the structural element and a reference signal is measured using a reference beam projected on a reference point on the ear. The measurement signal is representative for relative positions of one or more of the multiple measurement points on the structural element during the vibrations, such that a displacement of a respective measurement point between two measurements may be determined on the basis of two measurements, wherein each measurement is representative for a relative position of the respective measurement point. However, an absolute position of the measurement points, for example an absolute position on the structural element, when vibrating forward and backward with respect to a rest position, may be unspecified. The reference signal is representative for the motion phase of the structural element itself, such that, instead of an acoustic measurement and/or control of an acoustic phase of the acoustic stimulus, the actual motion phase of the vibrating structural element may be determined.

The projections of the measurement beam and the reference beam are related in time, such that a motion phase represented in the reference signal provides a motion phase reference for the measurement signal. Therewith, for each measurement of a measurement signal at a measurement point, the respective motion phase can be determined, which is possible without the need to measure each measurement point during multiple acoustic periods or to link the acoustic source to the OCT device by a trigger signal.

Thus, as the respective motion phase of the structural element in a vibration motion may be represented in the reference signal for each measured measurement signal of a measurement point, the maximum vibration amplitude of the measurement points may be determined on the basis of the measurement signal and the reference signal, even if the maximum amplitude occurs at a motion phase for which no measurement signal is measured.

The vibration amplitude of the measurement points can be determined because the reference point has been selected in such a way that the reference signal is representative for a motion phase of the structural element. The reference measurement may be carried out at a reference point on the structural element or at a reference point on another structural element of which a relationship with respect to the structural element is known, for example if another structural element also vibrates according to the same acoustic period due to the construction of the ear.

As such, the maximum displacement with respect to its rest position, or vibration amplitude of a measurement point can be determined on the basis of the measurement signal and the reference signal, without the need to measure the respective measurement point during at least one full acoustic period.

An advantage of the present invention is that less measurements are required for a reliable determination of the respective vibration amplitudes of the measurement points, such that a large number of measurement points may be measured within a clinically acceptable timeframe. The large number of measurement points may span a relatively large surface or volume, such as substantially the whole middle ear, which may be measured much quicker, for example in less than 1 minute, whereas this would not have been possible in the past, and, if possible, would have required at least 30 minutes.

The invention may offer several additional advantages:

Firstly, the motion phase of the structural element may now be determined with high accuracy, since the number of samples with which the reference signal is measured on the reference point is independent of the number of samples with which the measurement signal is measured on a single measurement point. As such, the reference point may advantageously be measured longer than one acoustic period such that an appropriate number of samples may be measured, with which the motion phase may be determined precisely. On the other hand, a number of samples per measurement point may be different and is thus not bound to this constraint. As such, a measurement point may be measured much shorter than one acoustic period, The reference signal and the measurement signal may be measured exactly at the same time, i.e. without possible influences of the sound velocity. As a result, the accuracy of determined vibration amplitudes at the measurement points is higher than was previously possible.

By projecting a reference beam with the at least one OCT device, it is possible to optimise the projection location of the reference beam for a reliable measurement of the reference signal. The choice of measurement points may be mainly driven by the structural element of interest, but the reference point may be selected independently based on different criteria, for example a reference point may be selected on a highly reflective part of the structural element, or a reference point may be selected on a location on which the amplitude is relatively high, compared to amplitudes of the measurement points. For example, the reference beam may be projected on a reference point on the tympanic membrane, having a relatively high amplitude, and the measurement beam may be projected on measurement points on the stapes, having a relatively low amplitude with which it may normally be more difficult to measure the reference signal reliably.

As the measurement signal and the reference signal are measured separately, the measurement signal may be filtered on the basis of the reference signal when determining vibration amplitudes. The reference signal is representative for a motion phase of the structural element and may therefore be expected to represent a periodicity of the motion phase according to the acoustic period. Deviations of the motion phase away from the expected periodicity may represent distortion. Unwanted movements of the structural element, for example due to external sound stimuli, may be difficult to distinguish on the basis of a measurement signal alone, but the unwanted movements may, however, result in deviations in the reference signal away from the expected periodicity, such that they can be identified in the reference signal. This allows correction for unwanted movements in the measurement signal, for example by ignoring or adjusting the respective measurement signal.

Movement detection on the basis of periodicity is a new approach that is different from detecting movements on the basis of shifts of signal peaks in individual measurements in a measurement signal, such as a distance signal, wherein a (spatial) shift in signal peaks represents a movement. Movement detection on the basis of individual measurements implies that a movement of a measurement point is detected only when the movement is equal to or larger than a depth resolution of the OCT system. The depth resolution is calculated using the spectral resolution of an OCT light source and may, for example, be 10-50 μm. According to the invention, movements may be detected on the basis of deviations in expected periodicity of the reference signal and the actual periodicity of the reference signal. As such, motion artefacts, and very small movements may be detected on a nanometer scale.

Finally, it is possible to measure two separate signals using shared OCT components. This can be advantageous as some components of an OCT-system, such as the laser, may be relatively costly.

Thus, the invention allows for accurate determination of vibration amplitudes of multiple measurement points quickly and accurately, which may improve vibrographic measurements for users and patients.

The structural element of which vibration amplitudes are to be determined is located in the ear of a patient. The structural element measured with the OCT device can be any element in or on the ear in which vibrations can be generated, such as the eardrum, the hearing bones and other parts of the ear, for example the inner ear. The measurement points are located on the structural element, for example, on one of the ossicles or a part of the cochlea. In an embodiment, the structural element comprises the tympanic membrane. In other embodiments, the structural element may be the umbo, stapes, incus or the round or oval window or parts thereof.

The acoustic source is configured to generate an acoustic stimulus to induce vibrations of the structural element and may, for example, comprise a tone generator, a speaker or a bone conduction headset. Properties of the acoustic stimulus may be varied with the acoustic source. For example, sound intensity, sound pressure and a direction of the acoustic stimulus may be chosen such that the acoustic stimulus induces vibrations of the structural element. The acoustic stimulus is emitted at an acoustic frequency which determines the acoustic period.

It will be clear to the skilled person that in addition or alternative to an acoustic stimulus, vibrations of the structural element may be induced by another stimulus, such as by an air puff induced by a pneumatic source, and/or by multiple stimuli.

The at least one OCT device is configured to measure a measurement signal and a reference signal with a measurement beam and a reference beam, respectively. The OCT device may, in use, emit low-coherent light using a low-coherent light source. The emitted beam of low-coherent light may then be split in at least one internal OCT-reference beam, the measurement beam and the reference beam for measuring the measurement signal and the reference signal. Internal OCT as used herein is to be understood as being a functional part of the OCT-system, not necessarily being physically integrated in the OCT-system.

Alternatively, multiple OCT devices may be provided, for example wherein a first OCT device measures the measurement signal, and a second OCT device measures the reference signal.

The internal OCT-reference beam may be reflected by an internal OCT-reference arrangement, comprising a reflector arranged at internal OCT-reference distance.

The term "reflected" as used herein comprises reflected and backscattered.

The at least one OCT device may be configured to project the measurement beam on a measurement point, and to project the reference beam on the reference point.

The measurement beam may be projected on one of the measurement points during a measurement, for example an A-scan, and projected on another one of the measurement points during another measurement, for example another A-scan.

The reference beam may be projected on the reference point, for example while the measurement beam is projected on the measurement point. Thus, the reference signal may be measured simultaneously with the measurement of the measurement signal. In use, the measurement beam may be reflected by the one of the measurement points as a reflected measurement beam and the reference beam may be reflected by the reference point as a reflected reference beam. The reflected measurement beam and reflected reference beam may interfere with the at least one internal OCT-reference beam, such that interference may be detected by the OCT device to provide the measurement signal and the reference signal.

The processing unit is configured to determine vibration amplitudes of the measurement points on the basis of the measurement signal and the reference signal.

The processing unit may be configured to pre-process the measurement signal and/or the reference signal, for example through filtering, compression and/or fault correction, for example using fixed noise removal, numerical dispersion compensation, zero padding and/or windowing. Pre-processing of the measurement signal and/or the reference signal may remove noise that may degrade the quality of the signals.

An inverse Fourier transform may be applied to the measurement signal and/or the reference signal by the processing unit to extract real (Re) and imaginary (Im) components thereof. A phase represented in the measurement signal and/or a phase represented in the reference signal may be calculated by a tan(Im/Re). The respective phases vary due to Doppler shifts in the reflected measurement beam and/or the reflected reference beam as a result of motion of the measurement point and/or the reference point, respectively.

The processing unit may be configured to determine a relative position of the measurement points and/or of the reference point, for example by $y_{m,r}(N)=\theta_{m,r}(N)*\lambda/(4\pi n)$, wherein y is the relative position of respectively the measurement point (m) and/or reference point (r), N is a measurement number, $\theta(N)$ is the phase in radians of respectively the measurement point (m) and/or reference point (r), $\lambda$ is the central wavelength of the OCT device, in particular of the light source thereof, and n is the refractive index of the medium in which the structural element is measured, for example n=1 for air. The measurement number may start at N=0 and increase with 1 each measurement.

The processing unit may be configured to determine a timestamp for a measurement, for example for an A-scan. This way, a measurement of the measurement signal and a measurement of the reference signal may synchronised with each other according to the timestamp. The timestamps may be calculated for each reference signal measurement (N) by $t(N)=N*t_s$, wherein N is a measurement number, and wherein $t_s$ is the sweep time(s) of the at least one OCT device that measures the reference signal. The sweep time(s) may be calculated by 1/fs, wherein fs is the number of measurements per second.

The processing unit may be configured to determine a displacement of a measurement point between two relative positions (N, N+d), for example by $\Delta y=y(N+d)-y(N)$, wherein $\Delta y$ represents the displacement of the measurement point from a relative position y at measurement N to a new relative position at measurement N+d that is d measurements apart from measurement N.

In an embodiment, the processing unit is configured to determine a motion phase q of the structural element on the basis of the reference signal. The motion phase may be determined by $\varphi=Y_r(N=0)/A_r$, wherein $Y_r(N=0)$ is the position of the structural element with respect to its rest position during a first measurement N=0, and $A_r$ is a reference amplitude of the reference point. The reference amplitude may be determined upon measurement of the reference signal during multiple acoustic periods in order to improve accuracy, for example by applying a Fourier transformation to the reference signal. The motion phase is zero if the first reference signal is measured performed exactly at the onset of a vibration motion. Normally, the initial motion phase $\varphi$ may be non-zero since the start of the measurement in relation to the position of the oscillating structural element is arbitrary.

The processing unit may be configured to model the vibration motion of the structural element on the basis of the reference signal. In particular, a vibration motion model may be fitted on the basis of the acoustic frequency f of the acoustic stimulus, relative positions y(N) of the reference point, motion phase $\varphi$ and timestamps for the measurements N. For a sinusoidal vibration, the model may be fitted according to $y(N)=\sin(2\pi ft(N)+\varphi)$, wherein y is the relative position, N is the measurement number, f is the acoustic frequency in Hz, t(N) is the a timestamp and $\varphi$ is the motion phase of the structural element due to acoustic vibration.

In an embodiment, the processing unit is configured to determine a vibration amplitude of at least one of the measurement points on the basis of the displacement of the measurement point represented in the measurement signal, and the motion phase represented in the reference signal.

In an embodiment, the processing unit is configured to determine a vibration amplitude of at least one of the measurement points, on the basis of a measurement signal representative for at least two relative positions of the measurement point at an unspecified motion phase, and a reference signal representative for specifying the motion phase of the structural element. The specified motion phase may specify the phase of the vibrating structural element in a periodic cycle of the structural element at a first measurement (N=0) in radians, for example $0.25\pi$ or $0.5\pi$, in case of a sinusoidal acoustic stimulus Owing to the invention, a vibration amplitude may be determined for a measurement point at a motion phase for which no measurement signal for the respective measurement point has been measured.

A vibration amplitude of a measurement point may, for a sinusoidal stimulus for example, be determined according to $A_m=\Delta y_m/(\sin(2\pi ft(N+d)+\varphi)-\sin(2\pi ft(N)+\varphi))$. Herein, $A_m$ is the (maximum) vibration amplitude, $\Delta y_m$ is the displacement of the measurement point from the measurement signal determined according to $\Delta y=y(N+d)-y(N)$, f is the acoustic frequency in Hz, t(N) is the timestamp determined according to $t(N)=N*t_s$, and $\varphi$ is the motion phase of the reference point.

The processing unit may determine a vibration amplitude using a reference signal and a measurement signal representative for positions during at least two measurements of a respective measurement point. This way, measurement time is reduced. However, vibration amplitudes may also be determined on the basis of respective signals representative for positions during multiple measurements, for example 3 or more measurements. This way, the determined vibration amplitude may be more precise.

For example, multiple amplitudes $A_m$ may be obtained on the basis of displacements between the multiple measurements of a measurement point, for example a displacement between a first and second measurement, a second displacement between the second and a third measurement, and a third displacement between the first and the third measurement. The multiple amplitudes may be combined to determine a single vibration amplitude, for example by determining an average or a linear combination thereof.

In an embodiment, the measurement beam and the reference beam are optically connected. This way, the measurement beam and the reference beam may be optically related to each other, such that the relation between the measurement beam and the reference beam is established by the optical connection and may be more precise.

In an embodiment, the at least one OCT device is configured to measure the measurement signal with a first number of samples and the reference signal with a second number of samples, wherein the second number of samples of the reference beam at the reference point is larger than a number of samples of the measurement beam at the measurement points. A number of measurements per second may be equal for the measurement beam and the reference beam, but the measurement beam may be projected on another one of the measurement points each measurement, such that the first number of samples of each of the measurement points is lower than the second number of samples of the reference point. Measuring the reference signal at a higher number of samples may be advantageous to determine vibration amplitudes of multiple measurement points using a single reference beam.

The number of samples, as used herein, may refer to a number of measurements that is performed with the respective measurement beam projected on a measurement point or the reference point, respectively. In some embodiments, the number of measurements per second could also differ between the first and reference beam. In some embodiments, additional measurement beams may be projected by the OCT device for measuring additional measurement signals and/or reference signals.

In an embodiment, the at least one OCT device is configured to move the measurement beam to subsequently measure the measurement points while holding the reference beam to measure the same reference point during measurement of the measurement points. This way, a measurement signal may be obtained of multiple measurement points, while the same reference point provides a motion phase for each of the measurement points.

The at least one OCT device may comprise a tracking system to compensate for movements of the ear, such that the reference beam remains projected on the reference point.

For measuring the measurement signal, the measurement beam may be consecutively projected on subsequent measurement points, for example with each measurement, or first be projected on the same measurement point, for example during several measurements, and then be moved to the next measurement point.

In an embodiment, the at least one OCT device is configured to measure a first reference signal representative for a motion phase of a first section of the structural element at a first reference point and to measure a second reference signal representative for a motion phase of a second section of the structural element at a second reference point, and wherein the processing unit is configured to determine vibration amplitudes of the measurement points using the first reference signal and/or the second reference signal in dependence of locations of the respective measurement points with respect to the first section and the second section. This approach is especially advantageous when the motion phase of the structural element is not constant over the volume of the structural element. In that case, measuring a single reference point may not be precise for all measurement points. Additional precision may be provided by measuring a motion phase of a second reference point for at least one of the measurement points, which corresponds better to the actual movement phase of the respective measurement point.

The at least one OCT device may be configured to move the reference beam between the first reference point to measure the first reference signal and the second reference point to measure the second reference signal. In other embodiments, the multiple reference points may be measured using additional measurement beams.

In further embodiments, more than two reference points may be measured. This way additional precision may be provided in the reference signal for more than two sections of the structural element.

In an embodiment, the at least one OCT device is configured to emit the measurement beam and the reference beam simultaneously. This way, the measured reference signal may be representative for a precise motion phase of the structural element at the moment of measuring the measurement signal.

In addition or alternatively, other forms of synchronisation between the measurement beam and the reference beam may be used, such that the measurements are performed simultaneously.

In an embodiment, the at least one OCT device comprises a light source and the at least one OCT device is configured to emit the measurement beam and the reference beam with the same light source. The OCT device may comprise a beam splitter to split a light beam from the light source in multiple measurement beams that allow measurement of the reference signal and the measurement signal. By sharing the light source, the need to synchronise light source sweeps of multiple light sources for synchronous measurement of the reference signal and the measurement signal is removed. Furthermore, the system may be more efficient and costs of the system may be reduced.

In an embodiment, the OCT device comprises a beam splitter to split a light beam from the light source in multiple measurement beams with a 50:50 ratio. This way, an equal amount of light may be provided for the measurement beam and the reference beam. However, in other embodiments, the light beam from the light source may be split with a different ratio. For example, a more intense measurement beam may be advantageous if measurement points relate to low reflective part of the structural element than the reference point, and vice versa.

In an embodiment, the at least one OCT device comprises an internal OCT-reference arrangement, configured to provide a reflected OCT internal OCT-reference beam, wherein the device is configured to measure the measurement beam and the reference beam using the same internal OCT-reference arrangement. By sharing components, the system may be more efficient and costs of the system are reduced.

Alternatively, the measurement beam and the reference beam may each be provided with a separate internal OCT-reference arrangement. By having separate internal OCT-reference arrangements, internal OCT-reference distances of the measurement beam and reference beam may be different, which avoids crosstalk.

In a further embodiment, the at least one OCT device comprises a first detector for detecting interference between the reflected internal OCT-reference beam and a reflection of the measurement beam, which defines a first internal OCT-reference arm and a first measurement arm, and a second detector for detecting interference between the reflected internal OCT-reference beam and a reflection of the reference beam, which defines a second internal OCT-reference arm and a second measurement arm, wherein optical path lengths of the first measurement arm and the first internal OCT-reference arm, respectively the second measurement arm and the second internal OCT-reference arm, are equal to each other. This way, the reflected measurement beams may interfere with the respective reflected OCT internal OCT-reference beam, such that interference can be detected and the measurement signal and the reference signal can be measured.

In a further embodiment, the optical path lengths of the respective first arms are different from the optical path lengths of the respective second arms.

It has been found that using a shared internal OCT-reference arrangement, at equal arm lengths, may cause crosstalk between the reference signal and measurement signal. This may be unwanted as it adds noise and induces additional interference. By elongating the second measurement arm and the second internal OCT-reference arm with respect to the first measurement arm and the first internal OCT-reference arm, or vice versa, crosstalk between the respective second and first arms may be reduced and/or eliminated. The optical path length may, for example by elongated by introducing additional fibres in the first or second arms, wherein the respective measurement arm and the internal OCT-reference arm remain approximately equal to each other.

In a further embodiment, one of the first measurement arm or second measurement arm is elongated with a length L, for example by introduction of a fibre having a length L, and the respective first internal OCT-reference arm or second internal OCT-reference arm is elongated with twice the length, thus 2L. As a light beam may travel twice through the respective measurement arm, i.e. in direction to the measurement point as measurement beam or to the reference point as reference beam and in opposite direction reflected from the measurement point as reflected measurement beam or from the reference point as reflected reference beam, the elongation of the first measurement arm or second measurement arm is advantageously half that of the respective internal OCT-reference arm.

In an embodiment, an optical path length difference of the second measurement arm and the second internal OCT-reference arm with respect to the first measurement arm and the first internal OCT-reference arm is larger than the imaging depth of the OCT device, for example larger than 4 times the imaging depth of the OCT device. This way, crosstalk may be reduced for reliable measurements of the reference signal and the measurement signal.

In an embodiment, the measurement beam and the reference beam are emitted towards the structural element via a single probe through a beam splitter or prism. The system according to the present invention allows for integration of the first and reference beam. By having a single probe, the system may be more efficient, vibration amplitudes may be determined quicker and comfort for patients and users may be improved.

The present invention provides a method for determining vibration amplitudes of a structural element of the ear, comprising the steps of:

generating an acoustic stimulus to induce vibrations of the structural element;

measuring a measurement signal representative for relative positions of multiple measurement points on the structural element during the vibrations;

measuring a reference signal representative for a motion phase of the structural element at a reference point; and determining vibration amplitudes of the measurement points on the basis of the reference signal and the measurement signal, wherein the measurement beam and the reference beam are related in time, such that a motion phase represented in the reference signal provides a motion phase reference for the measurement signal.

By measuring the reference signal at a reference point, a measurement signal may be measured at multiple measurement points. As the motion phase is represented in the reference signal, the measurement signal may be used to determine vibration amplitudes for a specific measurement points at other timestamps, for example the timestamp at which the vibration amplitude would be maximal, the vibration amplitude.

Vibration amplitudes may, for example, be determined using a reference signal and measurement signal representative for at least two measurements of a respective measurement point. This way, vibration amplitudes may be calculated by dividing the displacement between two relative positions by a sinusoidal reconstruction of the vibration motion on the basis of the reference signal.

This way, it is no longer required to measure each measurement point during multiple acoustic periods, such that measurement time is reduced and vibration amplitudes of larger surfaces of the ear may be measured.

In an embodiment of the method, the step of measuring a measurement signal is performed using a measurement beam projected on the multiple measurement points by at least one OCT device and wherein the step of measuring a reference signal is performed using a reference beam projected on the reference point by the at least one OCT device.

In an embodiment of the method, the structural element is a structural element of the middle or inner ear, and the reference point is located on another structural element of the ear.

The method may be suited for determining vibration amplitudes of a structural element of the ear, for example of middle or inner ear. The method further provides advantages similar to the advantages of the system, as described above.

The present invention further entails the use of a device according to any of the claims 1-12 for measuring acoustic vibrations of a structural element of the ear.

BRIEF DESCRIPTION OF THE DRAWINGS

Further characteristics and advantages of the invention will now be elucidated by a description of embodiments of the invention, with reference to the accompanying drawings, in which.

DETAILED DESCRIPTION OF EMBODIMENTS

Figures 1, 2A, 2B:
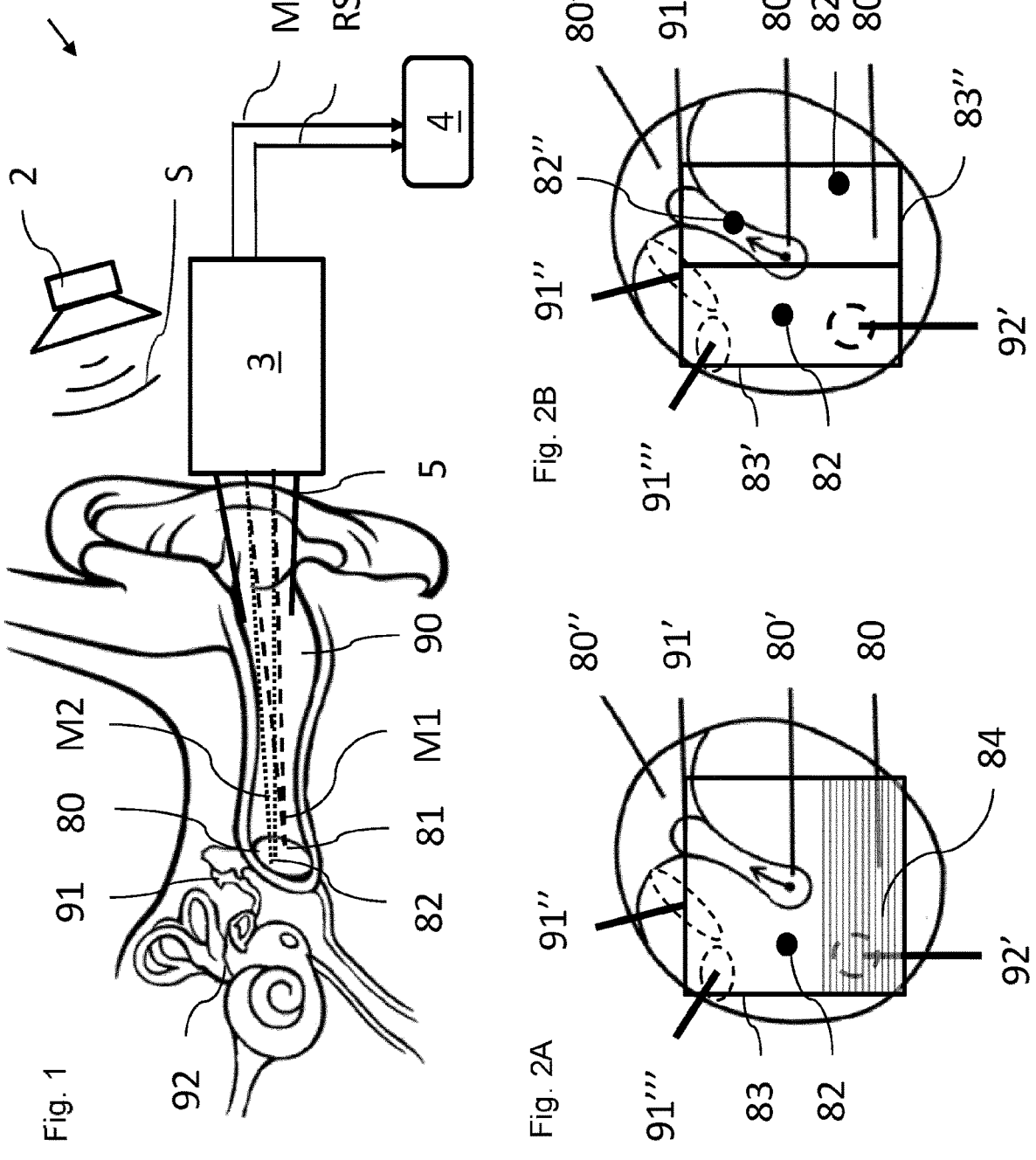
FIG. 1 schematically depicts an embodiment of a system for determining vibration amplitudes of a structural element of the ear.
FIGS. 2A and 2B schematically depict projection patterns of a measurement beam and a reference beam on a structural elements of the ear, according to two embodiments of the invention.

FIG. 1 schematically depicts an embodiment of a system 1 for determining vibration amplitudes of a structural element 80 of the ear, such as the tympanic membrane depicted in FIGS. 2A and 2B.

The system 1 comprises an acoustic stimulator 2, configured to generate an acoustic stimulus S to induce vibrations of the structural element 80. In this embodiment, the acoustic stimulus S is a sinusoidal acoustic stimulus having an acoustic period p.

The system further comprises an OCT device 3, configured to measure a measurement signal MS during the vibrations by projecting a measurement beam M1 on the measurement points 81 in a measurement, for example a first A-scan with the measurement beam. The measurement signal MS represents phases of the measurement points 81 that represent their relative positions, such that a displacement of a measurement point between to measurements may be determined on the basis of two measurements of that measurement pont.

The OCT device 3 is configured to measure at a reference point 82 a reference signal RS representative for a motion phase of the structural element 80 by projecting a reference beam M2 on the reference point 82 in the measurement, for example a second A-scan with the reference beam.

The projections of the measurement beam M1 and the reference beam M2 are related in time, such that a motion phase represented in the reference signal provides a motion phase reference for the measurement signal.

Figure 3B:
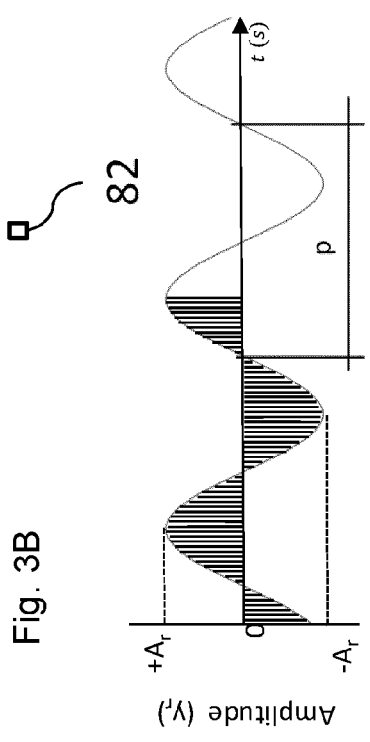
FIG. 3B schematically depicts the measurements of a reference signal according to an embodiment of the invention.

The OCT device 3 is configured to project the measurement beam M1 on each of the measurement points 81, such that the measurement signal MS is measured with a first number of samples, resulting in, for example, at least two samples per measurement point 81. The measurement beam M1 may be moved by the OCT device 3 to subsequently measure all measurement points 81. The measurement points 81 may span a section 83 of the structural 80, wherein the section 83 may comprise a relatively large surface or volume of the structural element 80. As depicted in FIG. 2A, the measurement beam M1 may be moved over the section 83 along images lines 84, wherein the image lines are formed by rows of measurement points 81, as depicted in FIG. 3A. Additionally or alternatively, the measurement beam M1 may be moved over the section 83 in a different fashion, such as in other patterns or randomly.

The OCT device 3 is configured to project the reference beam M2 on the reference point 82 once during each projection of the measurement beam M1 on one of the measurement points 81, such that a second number of samples of the reference beam M2 at the reference point 82 is larger than a number of samples of the measurement beam M1 at the measurement points 81.

In an embodiment, as depicted in FIG. 2A, the reference beam M2 is held to be projected on the reference point 82 to measure the same reference point 82 during measurement of the measurement points 81. The at least one OCT device 3 may comprise a tracking system to compensate for movements of the ear, such that the reference beam M2 remains projected on the reference point 82 during each measurement.

In another embodiment, as depicted in FIG. 2B, the multiple sections 83' 83" of the structural element 80 are measured. The OCT device 3 is configured to measure a first reference signal representative for a motion phase of a first section 83' of the structural element 80 at a first reference point 82 and to measure a second reference signal representative for a motion phase of a second section 83" of the structural element 80 at a second reference point 82'. Additionally, more reference points 82" may selected for additional sections of the structural element 80. In this embodiment, the OCT device 3 may be configured to move the reference beam between the first reference point 82 to measure the first reference signal and the second reference point 82' to measure the second reference signal.

The OCT device comprises a probe 5. The probe 5 may comprise a ear speculum that is configured to be inserted in to an ear, for example into an ear canal 90 of a patient.

The system further comprises a processing unit 4, configured to determine vibration amplitudes of the measurement points 81 on the basis of the reference signal RS and the measurement signal MS, In particular, the processing unit 4 is configured to determine a vibration amplitude of at least one of the measurement points 81, on the basis of a measurement signal MS representative for at least two relative positions of the measurement point 81 at an unspecified motion phase and a reference signal RS representative for the motion phase of the structural element 80. In this embodiment, the motion phase specifies the phase of the vibrating structural element in a periodic cycle of the structural element at a first measurement (N=0). In other words, the motion phase specifies a phase of the vibrating structural element 80 at the moment (t=0) of the first measurement (N=0). As such, the processing unit 4 is configured to determine vibration amplitudes A of the measurement points 81. For example, for a sinusoidal vibration, this motion phase may be 0.25π or 0.5π.

The processing unit is configured to pre-process the measurement signal and the reference signal through filtering, compression and/or fault correction, for example using fixed noise removal, numerical dispersion compensation, zero padding and/or windowing.

The processing unit is configured to determine a relative position of the measurement points and/or the reference point, a timestamp for each measurement, a displacement of a measurement point between two measurements of that measurement point and the motion phase of the structural element 80 on the basis of the reference signal RS.

In the embodiment of FIG. 2B, the processing unit 4 is configured to determine vibration amplitudes of the measurement points 81 in a similar way using the first reference signal and/or the second reference signal. Any combination of the first reference signal and the second signal may be used in dependence of locations of the respective measurement points 81 with respect to the first section 83' and the second section 83".

In use, the acoustic stimulus 2 is activated to generate an acoustic stimulus S having an acoustic period p to generate vibrations V of the structural element 80. An example of a vibration motion of a reference point 82 is depicted in FIG. 3B.

The section 83 of the structural element 80 may comprise the tympanic membrane (pars tensa), as depicted in FIGS. 2A and 2B, but may additionally or alternatively also comprise other parts of the ear, such as the umbo 80', pars flaccida 80", ossicles as the malleus 91', incus 91" or stapes 91''', the round window 92' and/or parts of the inner ear 92.

A measurement beam M1 is projected on measurement points 81 by the OCT device 3 to measure a measurement signal MS representative for the positions of measurement points 81 on the structural element 80. The MS measurement signal may comprise a phase $\theta_m$ for each measurement of the respective measurement points 81, as depicted in FIG. 3A.

A reference beam M2 is projected on the reference point 82 by the OCT device 3 to measure a reference signal RS representative for a motion phase of the structural element 80. The reference signal RS may comprise a phase $\theta_r$ for each measurement of the reference point 82. On the basis of the phase Or a relative position $y_r$ of the reference point may be determined, which is depicted in FIG. 3B.

The OCT device 3 may, for example, perform measurements with a sampling density of 100 000-400 000 measurements per second with the measurement beam M1 for multiple measurement points 81. The OCT device 3 may, for example, perform measurements at a reference point 82 with the same sampling density, such that the number of samples of the reference beam M2 at the reference point 82 is larger than the number of samples of the measurement beam M1 at one of the measurement points 81.

Figure 3C:
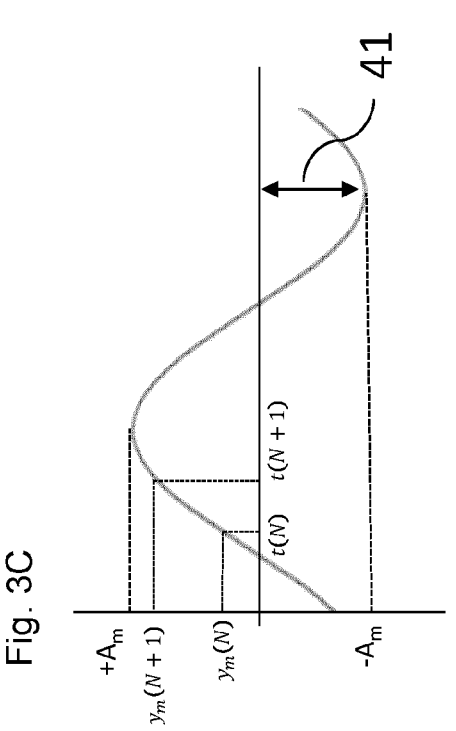
FIG. 3C schematically depicts the determination of vibration amplitudes on the basis of the measurement signal and the reference signal according to the embodiments of FIGS. 3A and 3B.
Figure 3A:
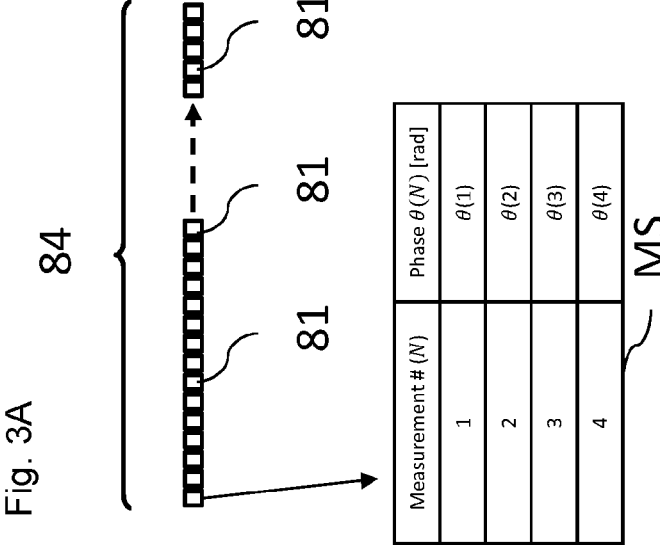
FIG. 3A schematically depicts the measurements of a measurement signal according to an embodiment of the invention.

Vibration amplitudes $A_m$ 41 of the measurement points are determined on the basis of the reference signal RS and the measurement signal MS, as depicted in FIG. 3C.

By the processing unit, an inverse Fourier transform is applied to the measurement signal MS and to the reference signal RS to extract real (Re) and imaginary (Im) components thereof. A phase $\theta_m$ is calculated from the measurement signal for each measurement of the measurement beam M1, for example by $\theta_m$=a tan(Im(MS)/Re(MS)). A phase $\theta_r$ is calculated for each measurement of the reference beam M2, for example $\theta_r$=a tan(Im(RS)/Re(RS)).

A relative position $y_m$ of a measurement point 81 during a measurement N is calculated by the processing unit 4 through $y_m(N)=\theta_m*\lambda/(4\pi n)$, wherein N is the measurement number, $\theta_m$ is the phase in radians, λ is the central wavelength of the OCT device 3, in particular of the light source thereof, and n is the refractive index of the medium in which the structural element is measured, for example n=1 for air. Similarly, a relative position $y_r$ of the reference point during a measurement N is calculated by the processing unit 4 through $y_r(N)=\theta_r*\lambda/(4\pi n)$. The measurement number starts at N=0 and increases with 1 each measurement.

A timestamp t of a measurement (N) is calculated by $t(N)=N*t_s$, wherein N is the measurement number and wherein $t_s$ is the sweep time(s) of the at least one OCT device 3 that measures the reference signal RS. The sweep time(s) is calculated by 1/fs, wherein fs is the sweep rate of the at least one OCT device 3.

Displacements Δy of a measurement point 81 between two measurements (N, N+d) of that measurement point 81 are calculated by $\Delta y_m=y_m(N+d)-y_m(N)$, wherein $y_m$ is the relative position of the measurement point 81 during a measurement and wherein a first measurement N and a subsequent measurement N+d of the respective measurement point 81 are located at a difference d measurements apart.

An motion phase φ of the structural element 80 during a first measurement is determined on the basis of the reference signal RS by the processing unit 4. The motion phase may be determined by $\varphi=y_r(N+0)/A_r$, wherein $y_r(N=0)$ is a relative position of the structural element during a first measurement, and $A_r$ is the vibration amplitude of the reference point, for example computed by fitting a vibration motion model on the basis of the reference signal and/or by a Fourier transform of the reference signal RS.

A vibration motion model is fitted on the basis of the acoustic frequency f of the acoustic stimulus, relative positions $y_r(N)$ of the reference point, the motion phase φ and the timestamps for the measurements N. For a sinusoidal vibration, the model may be fitted according to $y(N)=\sin(2\pi ft(N)+\varphi)$, wherein y is the relative position, N is the measurement number, f is the acoustic frequency in Hz and t(N) is the a timestamp and φ is the motion phase of the structural element due to acoustic vibration.

Then, vibration amplitudes $A_m$ of at least one of the measurement points 81 are calculated by the processing unit 4 on the basis of the displacement of the measurement point 81 that is represented in the measurement signal MS, and the motion phase φ represented in the reference signal RS according to $A_m=\Delta y_m/\sin(2\pi ft(N+d)+\varphi)-(\sin(2\pi ft(N)+\varphi))$, wherein $A_m$ is the (maximum) amplitude, $\Delta y_m$ is the displacement of the measurement point 81, f is the acoustic frequency in Hz and t(N) is the determined timestamp of the measurements N and N+d on the basis of which the displacement is calculated.

Figure 4:
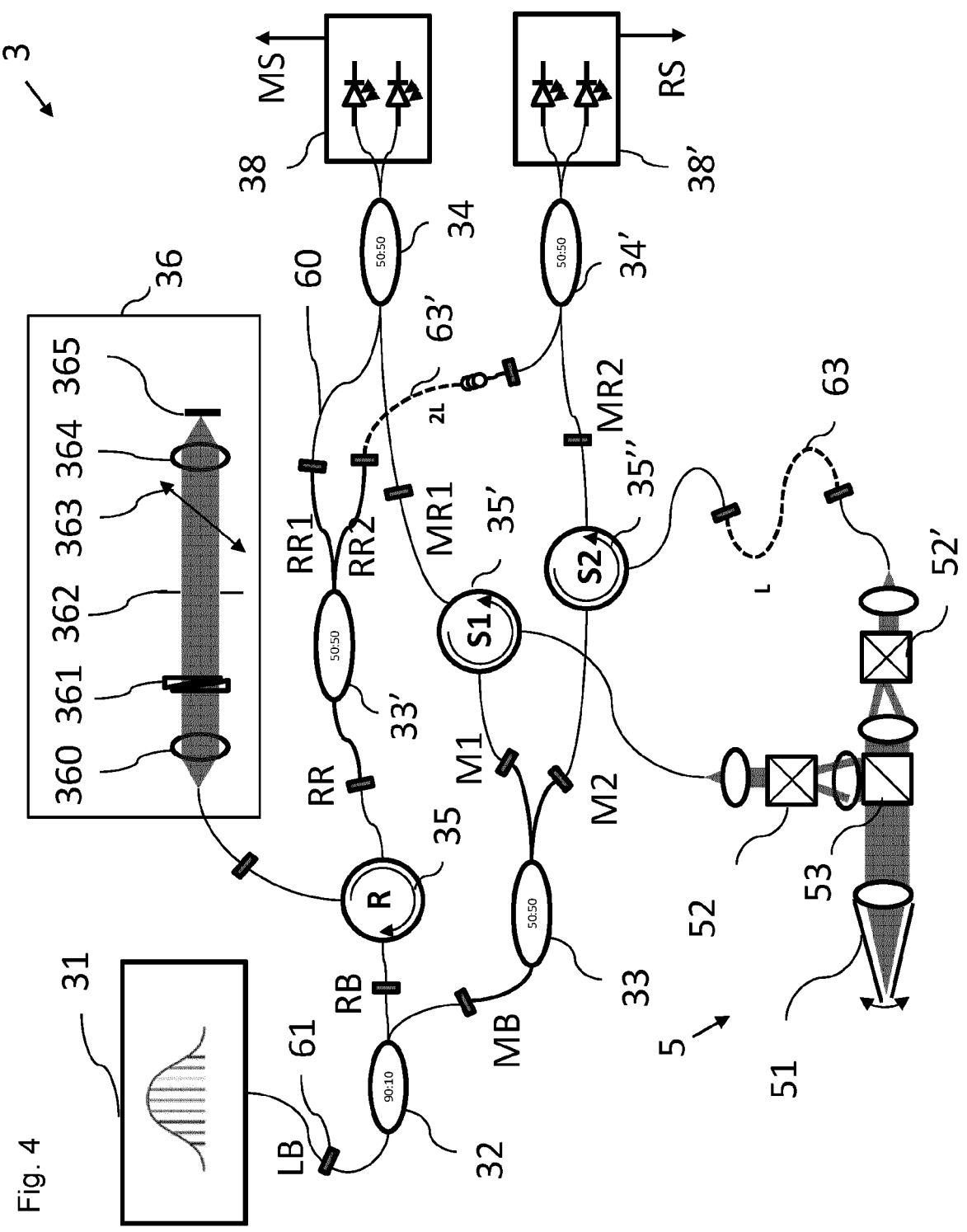
FIG. 4 schematically depicts an optical configuration of an OCT device according to an embodiment of the invention.

FIG. 4 schematically depicts an optical configuration of an OCT device 3 according to an embodiment of the invention. The OCT device 3 comprises various components, which, due to the specific configuration, enable the simultaneous measurement of a measurement signal MS with a measurement beam M1 and a reference signal RS with a reference beam M2. As such, vibration amplitudes of the measurement points 81 may be determined very reliably on the basis of the reference signal RS and the measurement signal MS.

The components comprise several components, such as splitters 32 33 33' 34 34' and selective nodes 35 35' 35" 35''', such as circulators R S1 S2. The components are, in this embodiment, optically connected via optical fibres 60 coupled with FC/APC connectors 61. In other embodiments, the components may be optically connected via other suitable means, such as other connectors.

The OCT device 3 comprises a light source 31 for emitting a low-coherent light beam LB. For example, the light source may emit a light beam with a central wavelength of 1300 nm, and a spectral bandwidth of 60 nm. The light beam LB is split in at least one measurement beam MB and at least one internal OCT-reference beam RB by a first splitter 32, in a ratio of 90:10. This ratio has been found to provide a convenient signal strength. However, the MB:RB ratio may be different, for example 99:1, 75:25 or 50:50.

The OCT device 3 comprises an internal OCT-reference arrangement 36, configured to provide a reflected internal OCT-reference beam RR. The internal OCT-reference arrangement 36 may comprise a collimator 360, a dispersion compensator 361, an intensity controller 362, a polarisation controller 363, a focusing lens 364, and a reference reflector 365 arranged at internal OCT-reference distance. The reference reflector provides a reflected internal OCT-reference beam RR, which, via a selective node 35 and a reference splitter 33' is provided as RR1 and RR2 to detectors 38 38', respectively. The RR1:RR2 ratio of the reference splitter 33' is 50:50, such that an equal amount of light is provided to both detectors 38 38'.

The detector 38 provides the signals which form the measurement signal MS and the detector 38' provides signals that form the reference signal RS.

As such, the OCT device 3 is configured to measure the measurement beam M1 and the reference beam M2 using the same internal OCT-reference arrangement 36.

The measurement beam and the reference beam are optically connected.

The measurement beam MB is split by a second splitter 33 in at least a measurement beam M1 and a reference beam M2. Via selective nodes 35' 35", the respective measurement beams are provided to the probe 5 such that they can be projected onto the ear of a patient.

The measurement beam M1 may be reflected on the ear of the patient by one of the measurement points 81 as a reflected measurement beam MR1 and the reference beam M2 may be reflected on the ear of the patient by the reference point 82 as a reflected reference beam MR2.

The probe comprises a first scanner 52 for the measurement beam M1 and the reflected measurement beam MR1, and a second scanner 52' for the reference beam M2 and the reflected measurement beam MR2. The respective measurement beams are emitted via ear speculum 51 after passing a beam splitter 53.

As such, the OCT device 3 is configured to emit the measurement beam M1 and the reference beam M2 with the same light source 31. The OCT device 3 is configured to emit the measurement beam M1 and the reference beam M2 simultaneously such that the measurements of the measurement signal MS and the reference signal RS may be performed simultaneously.

The detectors 38 38' are balanced detectors, that receive the respective internal OCT-reference beams RR1, RR2, respectively, and reflected measurement beams MR1, MR2 respectively, via splitters 34 34'. The splitters 34 34' each comprise a 50:50 ratio, such that light intensity at each detector in the balanced detector 38 38' is balanced e.g. ideally equal. Interference between the first reflected measurement beam MR1 and reflected internal OCT-reference beam RR1 may take place when the two beams are combined in splitter 34, and interference between the second reflected measurement beam MR2 and reflected internal OCT-reference beam RR2 may take place when the two beams are combined in splitter 34'.

An optical path between splitter 32, via the internal OCT-reference arrangement 36 to splitter 34 defines a first internal OCT-reference arm and an optical path between splitter 32, via the probe 5 to splitter 34 defines a first measurement arm. Similarly, optical paths via the internal OCT-reference arrangement 36 and the probe 5 to splitter 34' defines a second internal OCT-reference arm, respectively a second measurement arm.

Optical path lengths of the first measurement arm and the first internal OCT-reference arm, respectively the second measurement arm and the second internal OCT-reference arm, are equal to each other, such that interference can be detected by the detectors 38 38'.

The second measurement arm is elongated with a length L, for example by introduction of a fibre 63 having a length L, and the second internal OCT-reference arm is elongated with twice the length, thus 2L, for example by introduction of additional fibre 63'. Therewith, the optical path length of the first measurement arm is different from the optical path length of the second measurement arm.

As a light beam travels twice through the second measurement arm, i.e. as a reference beam M2 and as a reflected measurement beam MR2, the elongation L of the second measurement arm is half the elongation 2L of the second internal OCT-reference arm.

In this embodiment, the optical path length difference of the second measurement arm and the second internal OCT-reference arm with respect to the first measurement arm and the first internal OCT-reference arm is larger than an imaging depth of the OCT device 3, for example larger than 4 times the imaging depth of the OCT device 3.

The second splitter 33 has a M1:M2 split ratio of 50:50. However, other ratios may be used, such that more light may be directed to the measurement points or the reference point, if desired. This may be advantageous for measuring measurement and/or reference points that are located at larger distances with respect to the probe 5.

The measurement beam MB is split by splitter 33 before selective nodes 35' 35", such that the reflected measurement beams MR1 MR2 arrive undivided from the probe 5, via the respective selective nodes 35' 35' at the detectors 38 38', such that a reduction in signal strength is minimised.

Figure 5:
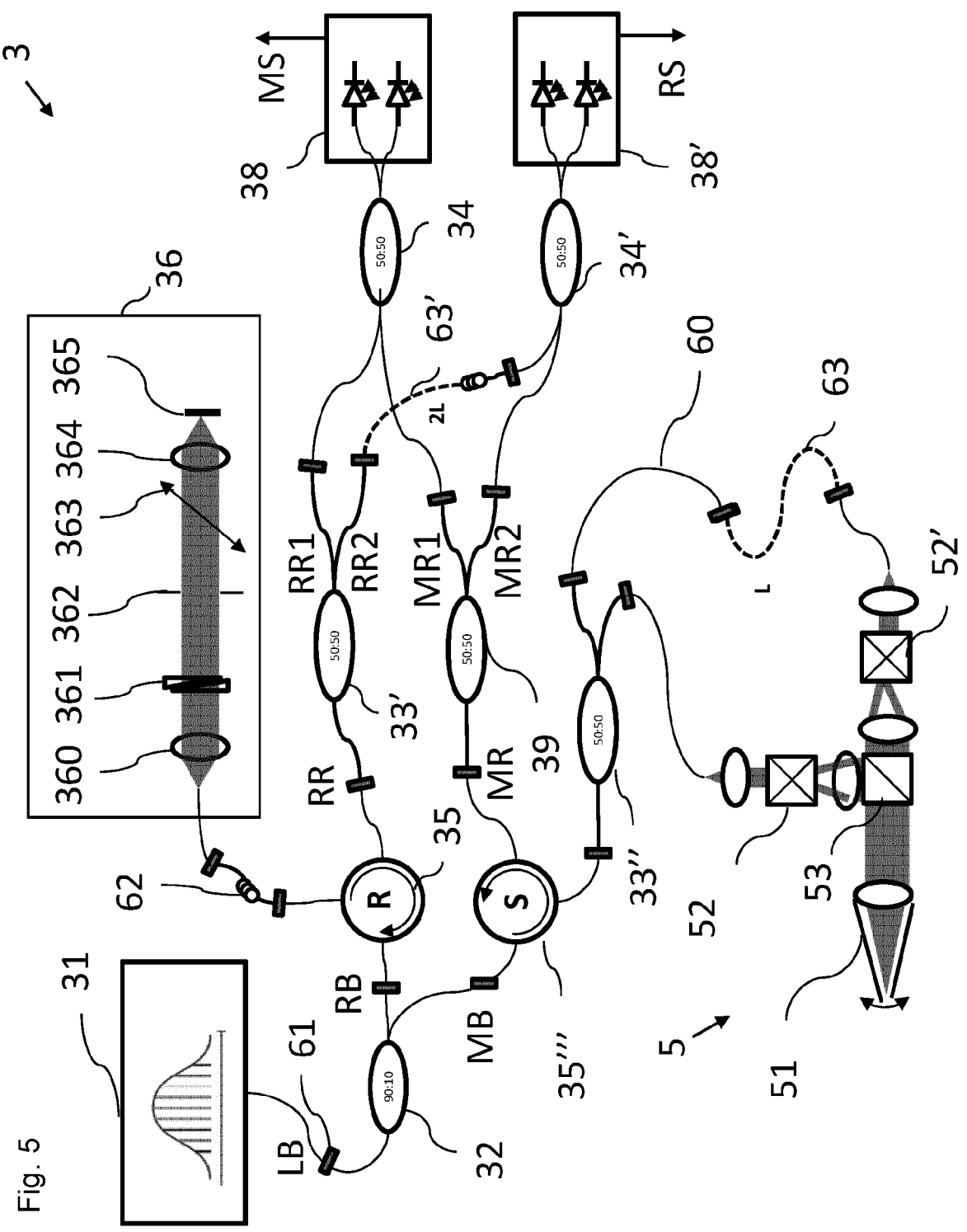
FIG. 5 schematically depicts an optical configuration of an OCT device according to another embodiment of the invention.

In FIG. 5, the measurement beam MB is split by the splitter 33" after the selective node 35'''. As such, less selective nodes are required, such as circulator S. In this embodiment, an additional splitter 39 is required in the measurement arms for splitting the reflected measurement beam MR into a first reflected measurement beam MR1 and a second reflected measurement beam MR2.

The additional splitter 39 has a splitting ratio 50:50, which will result in 50% reduction in signal strength. However, when the optical path length of the first measurement arm is sufficiently different from the optical path length of the second measurement arm, no interference between the first measurement arm and the second measurement arm will occur.

As the additional splitter 39 will result in an increased path length of the first measurement arm and the second measurement arm, both the first internal OCT-reference arm and the second internal OCT-reference arm are elongated according to the increased path length, for example with elongation fibre 62.

Figures 6A, 6B:
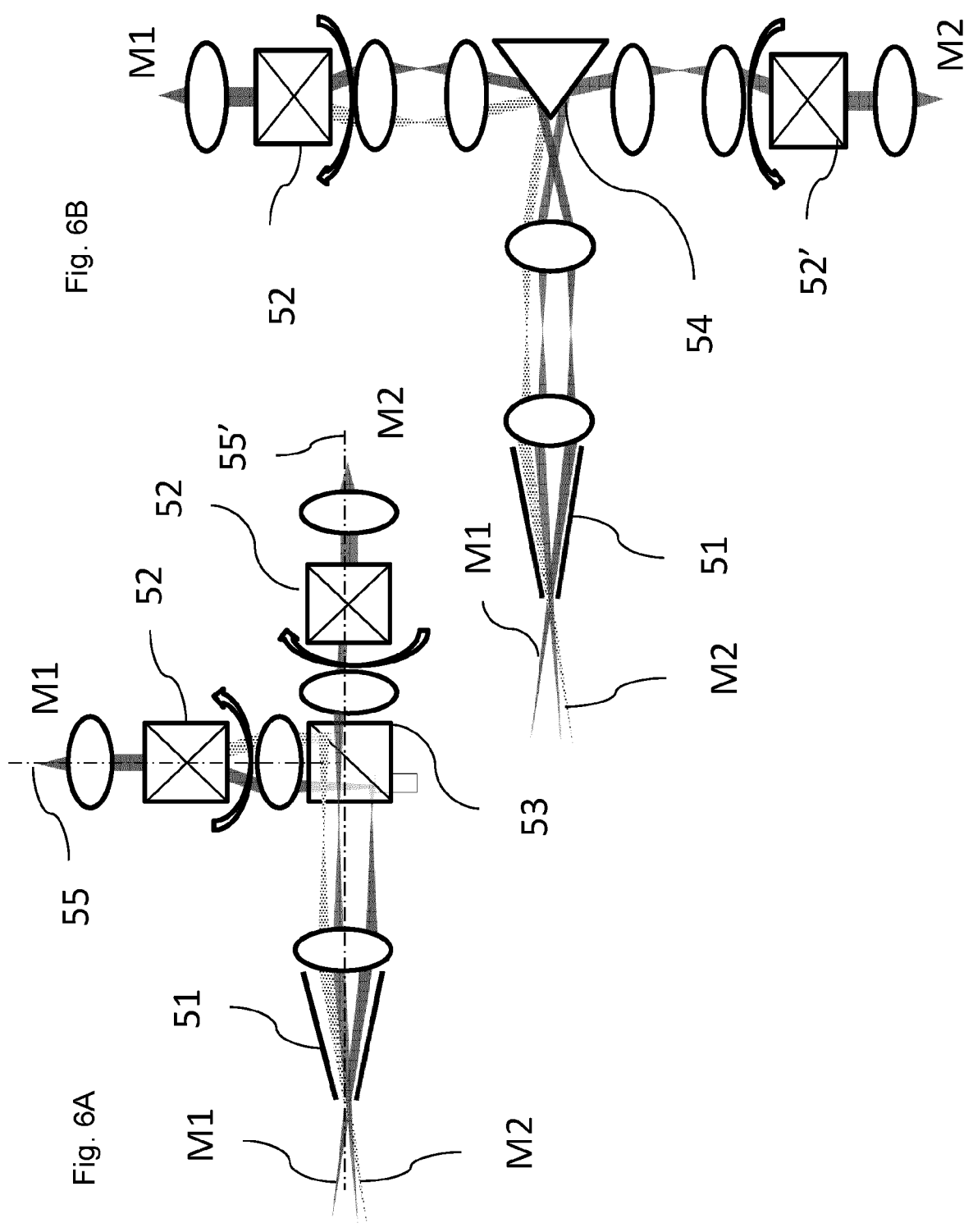
FIGS. 6A and 6B schematically depict configurations for projecting the measurement beam and the reference beam from a single ear speculum.

FIG. 6A depicts a probe according to the embodiments of FIGS. 4 and 5. The beam splitter 53 comprises a reflective surface having an optical coating that reflects and transmit incident light at a predefined ratio, such as 50:50. Upon passing the beam splitter 53, the central axes 55 55' of the measurement beam M1 and the reference beam M2 are coaxially aligned with each other.

FIG. 6B depicts a probe comprising a prism 54. In this configuration, a reflected measurement beam is passed to the first detector, and a reflected reference beam is passed to the second detector, such that less or no signal strength is lost.

In FIGS. 6A and 6B, the measurement beam M1 and the reference beam M2 are emitted towards the structural element via a single probe, in particular via a single ear speculum 51.

Figure 7:
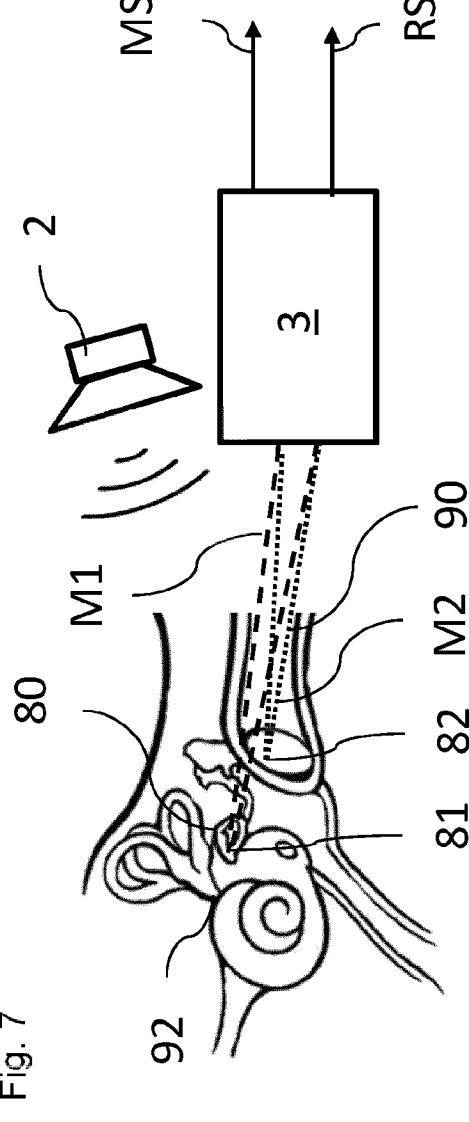
FIG. 7 schematically depicts an OCT measurement of a structural element of the middle ear, wherein the reference point is located on the tympanic membrane.

FIG. 7 schematically depicts an OCT measurement of a structural element 80 of the middle ear, wherein the reference point 82 is located on another structural element of the ear. The measurement point 81 is located on the stapes or oval window, and the reference point 82 is located on the tympanic membrane. A motion phase of the reference point is representative for a motion phase of the structural element.

The invention claimed is:

1. A system for determining vibration amplitudes of a structural element of an ear, the system comprising:

an acoustic stimulator configured to generate an acoustic stimulus having an acoustic period to induce vibrations of the structural element;

at least one optical coherence tomography (OCT) device configured to:

measure a measurement signal representative of relative positions of measurement points on the structural element during the vibrations by projecting a measurement beam on the measurement points; and measure a reference signal representative of a motion phase of the structural element with respect to the acoustic period by projecting a reference beam separate from the measurement beam on a reference point on the ear, wherein the measurement beam and the reference beam are each directed towards the ear; and a processing unit configured to determine vibration amplitudes of the measurement points on a basis of the reference signal and the measurement signal, wherein the projections of the measurement beam and the reference beam are related in time, such that a motion phase represented in the reference signal provides a reference for the measurement signal.

2. The system according to claim 1, wherein the processing unit is configured to determine a vibration amplitude of at least one of the measurement points on the basis of a displacement of the measurement point represented in the measurement signal, and the motion phase represented in the reference signal.

3. The system according to claim 1, wherein the processing unit is configured to determine a vibration amplitude of at least one of the measurement points, on the basis of a measurement signal representative for at least two positions of the measurement point at an unspecified motion phase, and a reference signal representative for the motion phase of the structural element.

4. The system according to claim 1, wherein the measurement beam and the reference beam are optically connected.

5. The system according to claim 1, wherein the at least one OCT device is configured to measure the measurement signal with a first number of samples and the reference signal with a second number of samples, wherein the second number of samples of the reference beam at the reference point is larger than a number of samples of the measurement beam at the measurement points.

6. The system according to claim 1, wherein the at least one OCT device is configured to move the measurement beam to subsequently measure the measurement points while holding the reference beam to measure the same reference point during measurement of the measurement points.

7. The system according to claim 1, wherein the at least one OCT device is configured to measure a first reference signal representative for a motion phase of a first section of the structural element at a first reference point and to measure a second reference signal representative for a motion phase of a second section of the structural element at a second reference point, and wherein the processing unit is configured to determine vibration amplitudes of the measurement points using the first reference signal and/or the second reference signal in dependence of locations of the respective measurement points with respect to the first section and the second section.

8. The system according to claim 1, wherein the at least one OCT device is configured to emit the measurement beam and the reference beam simultaneously.

9. The system according to claim 1, wherein the at least one OCT device comprises a light source and wherein the at least one OCT device is configured to emit the measurement beam and the reference beam with the same light source.

10. The system according to claim 1, wherein the at least one OCT device comprises an internal OCT-reference arrangement, configured to provide a reflected internal OCT-reference beam, wherein the OCT device is configured to measure the measurement beam and the reference beam using the same internal OCT-reference arrangement.

11. The system according to claim 10, wherein;

the at least one OCT device comprises a first detector for detecting interference between the internal OCT-reference beam and a reflection of the measurement beam;

the internal OCT-reference beam follows an optical path to the first detector that defines a first internal OCT-reference arm;

the measurement beam follows an optical path to the first detector that defines a first measurement arm and to a second detector for detecting interference between the internal OCT-reference beam and a reflection of the reference beam;

the internal OCT-reference beam follows an optical path to the second detector that defines a second internal OCT-reference arm;

the reference beam follows an optical path to the second detector that defines a second measurement arm;

optical path lengths of the first measurement arm and the first internal OCT-reference arm are equal to each other, respectively; and the optical path lengths of the second measurement arm and the second internal OCT-reference arm are equal to each other, such that interference can be detected and the measurement signal and the reference signal can be measured.

12. The system according to claim 11, wherein the optical path lengths of the first measurement arm and the first internal OCT-reference arm are different from the optical path lengths of the second measurement arm and the second internal OCT-reference arm.

13. The system according to claim 1, wherein the measurement beam and the reference beam are emitted towards the structural element via a single probe through a beam splitter or prism.

14. A method for determining vibration amplitudes of a structural element of an ear, the method comprising the steps of:

generating an acoustic stimulus to induce vibrations of the structural element;

measuring, using a measurement beam, a measurement signal representative for relative positions of measurement points on the structural element during the vibrations;

measuring, using a reference beam separate from the measurement beam, a reference signal representative of a motion phase of the structural element at a reference point with respect to the acoustic period; and determining vibration amplitudes of the measurement points on a basis of the reference signal and the measurement signal, wherein the measurement beam and the reference beam are each directed towards the ear, and wherein the measurement beam and the reference beam are related in time, such that a motion phase represented in the reference signal provides a motion phase reference for the measurement signal.

15. The method according to claim 14, wherein the step of measuring a measurement signal is performed using a measurement beam projected on the multiple measurement points by at least one optical coherence tomography (OCT) device and wherein the step of measuring a reference signal is performed using a reference beam projected on the reference point by the at least one OCT device.

16. The method according to claim 14, wherein the structural element is a structural element of the middle or inner ear, and wherein the reference point is located on another structural element of the ear.

* * * * *